United States Patent [19]

Lemelson et al.

[11] 4,321,929
[45] Mar. 30, 1982

[54] TOURNIQUET

[76] Inventors: Jerome H. Lemelson, 85 Rector St., Metuchen, N.J. 08840; Christian Grund, 2035 Burr Ave., Bronx, N.Y. 10461

[21] Appl. No.: 84,428

[22] Filed: Oct. 12, 1979

[51] Int. Cl.³ .............................................. A61B 5/00
[52] U.S. Cl. .................................... 128/630; 128/680; 128/691; 128/700; 128/736; 128/327
[58] Field of Search ................. 128/1 D, 24 R, 25 B, 128/325–327, 670–672, 677–683, 691–694, 700, 736

[56] References Cited

U.S. PATENT DOCUMENTS

| | | | |
|---|---|---|---|
| 3,552,383 | 1/1971 | Krueger et al. | 128/68 D |
| 3,942,518 | 3/1976 | Tenteris et al. | 128/24 R |
| 3,985,123 | 10/1976 | Herzlinger et al. | 128/1 D |
| 3,996,928 | 12/1976 | Maux | 128/683 |
| 4,106,002 | 8/1978 | Hogue, Jr. | 128/327 |
| 4,169,463 | 10/1979 | Piquard | 128/693 |
| 4,205,688 | 6/1980 | Hauser et al. | 128/694 |

OTHER PUBLICATIONS

Graham, M., "μP Checks EKG and Pressure", Electronic Design, 19, Sep. 13, 1976.

Primary Examiner—Robert W. Michell
Assistant Examiner—Francis J. Jaworski

[57] ABSTRACT

An automatic device, such as a tourniquet, and a control system therefor for arresting the flow of blood to the end of a limb, such as an arm or leg or a person. In one form, electronic sensing means senses one or more physiological variables of a patient to whose limb or body a tourniquet has been applied and generates signals which are applied to the inputs of a computer or microelectronic processor, which electrically processes and analyzes such signals and generates control signals for controlling the operation of one or more motors operating pumps for pumping fluid to cuff or restriction means such as a tourniquet to arrest the flow of blood therepast.

22 Claims, 3 Drawing Figures

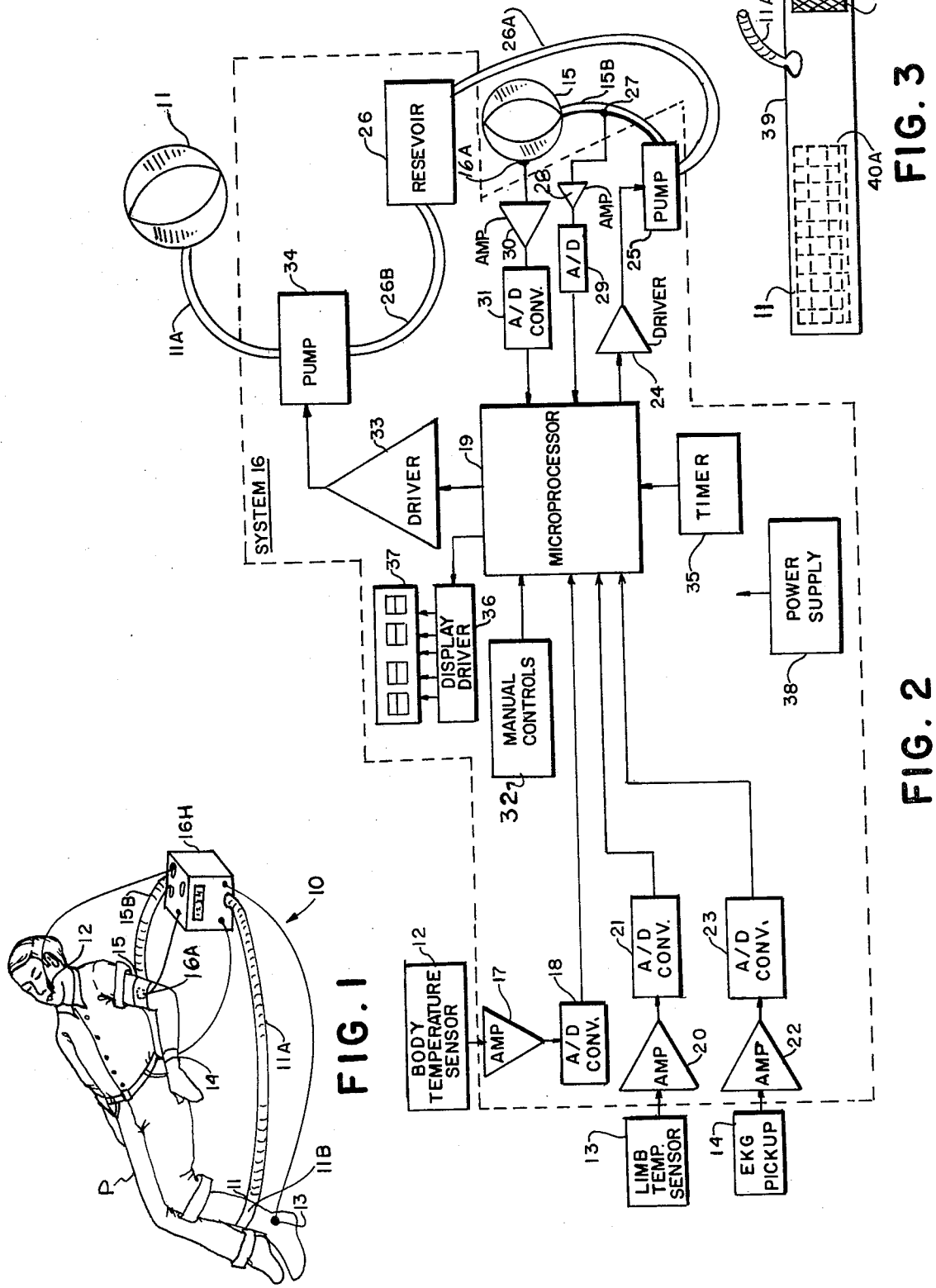

TOURNIQUET

SUMMARY OF THE INVENTION

This invention relates to an apparatus and method for restricting the flow of blood, particularly from a wound in the outer extremity of a human limb, and in particular to such an apparatus which may be automatically operated.

It is known in the art to provide pressure around a human limb to restrict or prevent the flow of blood from a wound. Flexible members or tourniquets wound around the limb and tightened, have been used to prevent excess bleeding from wounds which may be fatal if not restricted or stopped. However, tourniquets have certain shortcomings, a primary one of which is the fact that the inexperienced person utilizing such a device, may not properly adjust it against the limb and may improperly control or apply force to the limb which must be relieved from time to time to avoid causing permanent damage. As a result, if the tourniquet is so improperly applied and controlled, the patient may suffer tissue damage or excess loss of blood and possibly succumb due to such blood loss.

The instant invention provides an automatic control system for a tourniquet which may be automatically operated to apply and release pressure on a human limb in accordance with signals generated by one or more physiological sensors and electronic computing means for processing such signals, to determine when to apply and release force by adjustably operating the tourniquet and thereby apply and release pressure to the wound.

Accordingly it is a primary object of this invention to provide an apparatus and method for arresting or preventing the flow of blood from a wound.

Another object is to provide a method for automatically controlling the flow of blood between two portions of the human body.

Another object is to provide a variable tourniquet and an automatic control system therefor.

Another object is to provide a computer controlled apparatus for assuring that a wounded person does not suffer excess bleeding.

Another object is to provide a microprocessor controlled electronic system for use in controlling and operating a tourniquet applied to a human body, which system is light enough in weight to be easily transported.

Another object is to provide a microprocessor controlled system and a portable tourniquet apparatus controlled thereby for controlling the flow of blood to a wound, which system and apparatus is light enough in weight to be carried by a person, including a person whose blood flow is to be controlled so that it may be utilized in-the-field and carried along with the wounded person.

Another object is to provide a system and method for controlling the flow of blood in a human being in accordance with variations in one or more physiological parameters which are detected by one or more sensors which generate signals which are electronically processed and are utilized to effect such blood flow control.

With the above and such other objects in view as may hereinafter more fully appear, the invention consists of the novel constructions, combinations and arrangements of parts and the method employed in controlling the flow of blood, as will be more fully described and illustrated in the accompanying drawings, but it is to be understood that changes, variations and modifications may be resorted to which fall within the scope of the invention as claimed.

In the drawings:

FIG. 1 is a view of a patient and automatic tourniquet applied to the leg of a patient together with physiological sensing devices for providing signal information on the condition of the patient for a microcomputer and control means for inflating and deflating the tourniquet;

FIG. 2 is a schematic diagram showing electronic components including a microprocessor and fluidic pressure applying means for a tourniquet and blood pressure sensing means of the types shown in FIG. 1; and FIG. 3 is a face view showing details of a typical tourniquet of the type shown in FIG. 1.

In FIG. 1 is shown an automatic tourniquet system 10 applied to a patient P and defined by a tourniquet 11 which consists of an inflatable bladder 11B adapted to inflate when a fluid under pressure is applied thereto to cause pressure against the lower left leg of the patient. The patient also has a body temperature sensor 12, limb temperature sensor 13, heart signal EKG pickup 14, which sensors comprise suitable transducers such as a thermistor, photoelectric pickup or electrodes suitably connected or attached to the patient. A blood pressure cuff 15 is provided which contains an intrinsic microphone 16A connected to the body of the patient and extending to a pumping and control system 16 supported in a portable housing 16H.

In FIG. 2 is shown details of the pumping and control system 16. Signals received from the body temperature sensor 12 are amplified by an amplifier 17 and are converted to digital form by an analog-to-digital converter 18, the output of which is connected to an input of a microprocessor 19 to input the digitized analog information thereto. The signals generated by the limb temperature sensor 13 are amplified by an amplifier 20 and converted to digital form by an analog-to-digital converter 21, the output of which extends to another input of a microprocessor 19. The signals generated by the heart beat pickup 14 are also amplified by an amplifier 22, converted to digital form by an analog-to-digital converter 23 and are applied on another input to the microprocessor 19.

At regular intervals, signals generated on an output of microprocessor 19 which extends to a suitable drive circuit 24, are employed to control and effect the operation of a motor forming part of a pump module 25, which pump operates to draw suitable fluid from a reservoir 26 through a hose 26A and thereby inflates the blood pressure cuff 15 through hose 15B with a predetermined fluid pressure in accordance with the pressure sensed by a pressure sensor 27, the signals of which are amplified by an amplifier 28 and digitized by an analog-to-digital converter 29 which, in turn, applies such digital signals to the microprocessor 19 for processing and evaluation.

When the preset pressure level is reached, the microprocessor operates to deactivate driving circuit 24 and the motor for pump 25, allowing the fluid in cuff 15 to bleed back slowly through the pump to the fluid reservoir 26. Signals from microphone 16A are amplified by an amplifier 30 and digitized by an analog-to-digital converter 31, the output of which converter is continuously monitored and analyzed by circuits in the microprocessor 13 for automatically indicating and determining blood flow sounds picked up by the pressure sensor. When such sound signals are first generated by the pressure sensor 27, they are amplified by an amplifier 28 and converted to digital form by means of an analog-to-digital converter 29 connected to the amplifier, the output of which is a digital indication of systolic blood pressure and which is transmitted to the microprocessor 19 for processing. When the sound generated signals diminish, the microprocessor 19 commits to its memory or records the output of pressure sensor 27 which is indicative of the diastolic blood pressure of the patient. These pressure readings or signals are refreshed during predetermined time intervals and are held in the memory of the microprocessor for analysis between the blood pressure signal recording intervals.

A set of manual controls 32 may be preset by an operator, to record critical values of pressure, temperature or other physiological parameter in the memory of the microprocessor 19, at which values the tourniquet 11 is required to be tightened or released. The tightening of the tourniquet 11 is accomplished whenever the microprocessor 11 generates signals for activating the driver 33 which supplies operating power to the motor of the pump unit 34. The pump of the pump unit 34 then pumps suitable fluid from the reservoir 26 through a hose 26B and then through hose 11A to the cuff 11 of the tourniquet, which is similar in construction to the blood pressure cuff 15, so as to permit inflation of the former and the application of suitable pressure to the limb containing such cuff.

A timer 35 is connected to 19 for controlling same and providing intervals during which blood pressure is sensed and the tourniquet is tightened, other than those intervals determined by the sensed critical values of pressure and temperature.

If it is desired to provide a readout of the physiological parameters being monitored, microprocessor 19 has an output extending to a display driver 36 which operates or drives a digital electronic display 37 which may contain a number of light emitting diode or liquid crystal diode numerical display units. In FIG. 2, a suitable power supply 38 is provided which is operatively connected to all of the components of the system requiring electrical energy for their operation as described.

FIG. 3 illustrates a typical construction of the blood pressure cuffs 11 and 15 shown in FIGS. 1 and 2. The cuff is formed of an elongated flexible bladder 39, preferably made of a rubber or synthetic plastic or plastic coated cloth, which is filled with fluid, as previously described, through an input hose or flexible line 11A or 15B. Multielement textile fastening material in the form of patches 40A and 40B of so-called Velcro or the like, are secured to opposite ends of the cuff 11 to fasten the cuff firmly around the arm or leg of the user as illustrated in FIG. 1. A suitable adjustment type connection means, such as a buckle, may also be employed to variably secure the ends of the cuff tightly around the limb of a user or patient.

Modified forms of the instant invention include the following:

I. Two or more tourniquets may be employed to control blood flow to different limbs of a patient having wounds in said different limbs, each of which tourniquets may be controlled either simultaneously to prevent blood flow therepast by the means provided in FIGS. 1-3 or by respective systems such as system 16.

II. One or more pressure sensing cuffs such as blood-pressure sensing cuff 15 may also be operated to restrict or stop the flow of blood therepast in the manner of a tourniquet so as to serve both functions.

III. The described pressure sensing cuffs and/or tourniquets may also serve as supports for other sensing transducers such as the described temperature and EKG sensing transducers.

We claim:

1. An automatic tourniquet for use in arresting the flow of blood in a limb of a living being to prevent bleeding and loss of blood by said living being comprising in combination:

first means for compressively engaging the exterior portion of a human body limb and compressing blood vessels therein in a manner to restrict the flow of blood in said blood vessels extending through a portion of the limb engaged, second means for activating said first means to cause said first means to apply pressure to the exterior of said body limb, third means for deactivating said first means after it is activated by said second means to relieve pressure on said body limb, electrically operated control means for controlling said second and third means to selectively activate and deactivate said first means to compress and release pressure on said body limb engaged by said first means, sensing means for sensing a physiological variable and generating a signal which is indicative of said variable, computing means connected to receive signals from said sensing means and including signal processing means for processing the received signals and means for determining when the variable sensed exceeds a predetermined value and means for generating a control signal when such determination is made, means for applying said control signal to said control means to cause said control means to control said second means to cause said first means to compress and apply force against said body limb in accordance with the characteristics of the variable sensed so as to predeterminately arrest the flow of blood through said body limb.

2. An automatic tourniquet in accordance with claim 1 including sequential control means operable in response to signals generated by said computing and signal processing means for sequentially controlling said second and third means to compress and release pressure on said body portion engaged by said first means in a predetermined sequence.

3. An automatic tourniquet in accordance with claim 1 wherein said first means includes an inflatable member engaged against the exterior of said body limb.

4. An automatic tourniquet in accordance with claim 3 wherein said second means is operable to inflate said inflatable member to cause it to compressively engage said body limb and said third means is operable to effect inflatation of said inflatable member to relieve pressure against said body limb.

5. An automatic tourniquet in accordance with claim 4 wherein said first means comprises an inflatable band assembly defining a cuff and adjustable means for securing said cuff around the limb of a person.

6. An automatic tourniquet in accordance with claim 4 wherein said second means is a motor operated pump, conduit means connected to the input and output of said pump and to a reservoir for supplying fluid to said pump and conducting said fluid to said inflatable cuff disposed around said limb to cause said cuff to inflate and compress said limb, and valve means for holding fluid pumped into said cuff by said pump to retain said cuff compressing said limb, said third means including means for controlling said valve means to open and release fluid from said cuff to said reservoir.

7. An automatic tourniquet in accordance with claim 1 wherein said computing and signal processing means includes an electronic microprocessor.

8. An automatic tourniquet in accordance with claim 7 wherein said sensing means is operable to generate signals which are indicative of heart beat and said computing means is operable to detect when the pulse rate of a patient to whom said cuff is attached exceeds a given value.

9. An automatic tourniquet in accordance with claim 7 wherein said sensing means is operable to generate signals indicative of blood pressure and said computing means is operable to determine when blood pressure sensed by said sensing means is of such a value as to require a variation in the operation of said first means and generates signals for controlling operation of said first means and said second means in accordance with the blood pressure sensed by said sensing means.

10. An automatic tourniquet in accordance with claim 1 wherein said sensing means includes a plurality of sensors for sensing blood pressure, heart beat and temperature and said computing means is operable to analyze signals generated by said sensing means and to generate output control signals in accordance with computations performed by said computing means for controlling the operation of said second and third means so as to control said first means in compressing and releasing pressure against the body limb compressed by said first means.

11. An automatic tourniquet in accordance with claim 1 including alarm means for indicating when the variable sensed by said sensing means is at a predetermined value.

12. An automatic tourniquet in accordance with claim 11 including further alarm means for indicating a hazardous physical condition of a person requiring emergency treatment whose physiological variable is sensed by said sensing means.

13. A method of preventing bleeding from a wound comprising:
applying a tourniquet to a portion of the body of a person, which body portion is located between a wound and the heart of the person and is such that pressure applied thereto will restrict the flow of blood beyond the portion where pressure is so applied so as to prevent blood from flowing from the wound and wherein such tourniquet may be remotely controlled to apply and release pressure on the portion of the body against which the tourniquet is disposed,
sensing a physiological parameter, such as blood pressure, of the person to whom said tourniquet is applied and generating electrical signals which are indicative of variations in said parameter,
electronically processing said signals generated by such sensing, and
generating a control signal when the physiological parameter sensed reaches a preset value, and
applying said control signal to control the operation of said tourniquet to apply pressure against the portion of the body to which it is secured.

14. A method in accordance with claim 13 wherein said tourniquet is fluidically operated to apply and release pressure, and wherein said tourniquet is controlled in its operation by automatically applying fluid pressure thereto and releasing such fluid pressure in accordance with signals generated by said signal processing means.

15. A method in accordance with claim 14 wherein said control signal controls the operation of a pump applying fluid pressure to said tourniquet.

16. A method in accordance with claim 15 including deactivating the operation of said pump after it has applied fluid pressure to said tourniquet and permitting fluid applied to said tourniquet to bleed out of said tourniquet permitting said tourniquet to release its pressure against the portion of the body to which it is applied.

17. A method in accordance with claim 13 wherein the tourniquet is supported against the body of a person by means of a flexible band, said method further including supporting a sensor on said band in a manner to permit said sensor to sense said physiological variable and generate said signal.

18. A method in accordance with claim 13 wherein the signals generated by sensing the physiological parameter are electrically processed by digitizing same and the control signals are generated on the output of an electronic microprocessor receiving and analyzing such digital signals.

19. A method in accordance with claim 13 further including displaying an indication of the magnitude of the physiological parameter sensed.

20. A method in accordance with claim 13 wherein said tourniquet is applied to a body limb and is operable to stop the flow of blood therepast to the end of the limb.

21. A method of preventing bleeding from a wound comprising:
applying a tourniquet to a portion of a body of a person, which body portion is located between the wound and the heart of such person and is such that adequate pressure applied thereto will restrict the flow of blood beyond the portion of the body where such pressure is applied so as to prevent the blood from flowing from the wound, wherein such tourniquet may be automatically controlled to apply and release pressure on the portion of the body against which the tourniquet is disposed,
sensing a physiological parameter of the person to whom such tourniquet is applied and generating signals which vary in accordance with variations in said physiological parameter,
processing said signals generated by such sensing and generating control signals when the signals exceed a given value, and
automatically controlling the operation of said tourniquet with said control signals to apply and release pressure to the portion of said body to which said tourniquet is applied so as to restrict or stop the flow of blood across the body portion engaged by said tourniquet and to allow blood to flow thereacross at predetermined time intervals.

22. A method in accordance with claim 21 wherein the tourniquet includes an electrically controllable force applying means, and effecting automatic control by means of a timer controlled by said control signals for controlling operation of said electrically controllable force applying means.

* * * * *